United States Patent [19]

Hoffman et al.

[11] Patent Number: 4,656,083
[45] Date of Patent: Apr. 7, 1987

[54] PLASMA GAS DISCHARGE TREATMENT FOR IMPROVING THE BIOCOMPATIBILITY OF BIOMATERIALS

[75] Inventors: Allan S. Hoffman; Andrew Garfinkle; Buddy D. Ratner, all of King County, Wash.; Stephen R. Hanson, San Diego County, Calif.

[73] Assignee: Washington Research Foundation, Seattle, Wash.

[21] Appl. No.: 709,990

[22] Filed: Mar. 11, 1985

Related U.S. Application Data

[63] Continuation of Ser. No. 519,383, Aug. 1, 1983, abandoned.

[51] Int. Cl.⁴ .............................................. B05D 3/06
[52] U.S. Cl. .................................... 428/265; 427/2; 427/41; 428/422; 604/266; 128/DIG. 22
[58] Field of Search .................. 427/38, 39, 40, 41, 427/2; 3/1.4, 1.5, 1.7; 128/DIG. 22; 604/266, 408, 409, 410; 204/169; 428/265, 422

[56] References Cited

U.S. PATENT DOCUMENTS

| | | | |
|---|---|---|---|
| 3,817,701 | 6/1974 | Thorsen . | |
| 3,839,743 | 10/1974 | Schwarcz | 3/1.4 |
| 4,188,426 | 2/1980 | Averbach | 204/169 |
| 4,261,806 | 4/1981 | Asai et al. | 427/40 |
| 4,264,750 | 4/1981 | Anano et al. | 204/169 |
| 4,312,575 | 1/1982 | Peyman et al. | 427/41 |
| 4,488,954 | 12/1984 | Hatada | 204/169 |

FOREIGN PATENT DOCUMENTS 122529 7/1979 Japan .

OTHER PUBLICATIONS

Yanigihara et al. *J. Poly. Sc., Poly. Chem. Ed.*, V 20, pp. 1833-1846 (1982).
Kay et al. *J. Vac. Sci. Tech.*, vol. 18, pp. 1-18 (Jan., Feb. 1981).
Yasuda "Contemporary Topics in Polymer Science", vol. 3, Shen, Ed. Plenum Pub. Co., pp. 103-123 (1979).
Yasuda *J. Macromol. Sci. Chem.*, A10(3), pp. 383-420 (1976).
Salhi et al. *Thin Solid Films*, V 84, pp. 399, 400.
Anand et al. *Polymer*, V 22, pp. 361-371 (1981).
Corbin et al. *Polymer*, vol. 23, pp. 1546-1548 (1982).
Clark et al., *J. Poly. Sci., Poly. Chem. Ed.*, vol. 20, pp. 1717-1728 (1982).
Biederman *Vacuum*, vol. 31, No. 7, pp. 285-289 (1981).
Kay et al. *J. Appl. Phys.*, vol. 51, No. 11, pp. 5678-5687 (1980).
Yasuda Report PB-278 122 U.S. Dept. of Comm., Dec. 1977.
Yasuda Report PB-259 106, U.S. Dept. of Comm., Aug. 1976.
Baier et al., NIH Annual Report No. WO6-EB-53-07-MI (Feb. 1975).
Kodama et al. *Kobunshi Ronbunshu*, vol. 38, No. 10, pp. 725-731 (1981).
Yasuda "Annual Report to the NIH for Grant No. HL 244767-02 (1981-82).
Yasuda et al. *Biomaterials*, vol. 1, pp. 68-77 (1982).
Hahn et al. *ISA* (1981), pp. 109-113.
Morosoff et al., Report PB-80 212715, U.S. Dept. of Comm. (1980).

*Primary Examiner*—John H. Newsome
*Attorney, Agent, or Firm*—Seed and Berry

[57] ABSTRACT

A method of treating articles to improve their biocompatibility is disclosed. A substrate material is positioned within a reactor vessel and exposed to plasma gas discharge in the presence of an atmosphere of an inert gas and then in the presence of an organic gas, such as a halocarbon or halohydrocarbon gas, capable of forming a thin, biocompatible surface covalently bonded to the surface of the substrate. The method is particularly useful in the treatment of vascular graft materials to improve their biocompatibility.

15 Claims, 7 Drawing Figures

PLASMA GAS DISCHARGE TREATMENT FOR IMPROVING THE BIOCOMPATIBILITY OF BIOMATERIALS

This invention was made with government support under Grant No. HL22163 by the National Heart, Lung and Blood Institute, National Institute of Health.

This application is a continuation of U.S. patent application Ser. No. 519,383, filed Aug. 1, 1983, now abandoned under C.F.R. §1.62.

TECHNICAL FIELD

This invention relates to a method of improving the biocompatibility of biomedical articles and to such articles for use as dental and orthopedic implants, blood contacting devices for diagnosis or for therapy, including vascular prostheses, heart valves, etc.

BACKGROUND ART

Biomedical articles, particularly those which are in contact with blood, require certain properties to ensure acceptance by the body and body tissue for incorporation into the body on a long-term basis.

Prosthetic arterial replacements in humans to correct impaired arterial flow are well accepted. Grafts of polyester, tetrafluoroethylene and other synthetic materials are commonly used where the diameter of the arterial replacement is generally greater or equal to six millimeters; however, synthetic vascular prostheses with diameters less than six millimeters have not been conventionally employed, generally because of the increased probability of the development of obstructions due to thrombosis and/or vessel wall thickening.

The search for an ideal prosthetic arterial graft began some 25 years ago with research and development focusing on smooth-walled, non-thrombogenic "intert" implants. Ideas centered around Teflon and Dacron low porosity weaves which did not require preclotting as there was no blood leakage at surgery. Over the past 10 years more "reactive" or initially thrombogenic grafts have increasingly been used in surgical applications. Knits, external and finally internal velours appeared, all of which were porous, increasingly textured surfaces requiring preclotting. These seemed to be better incorporated into the body on a long term basis both in terms of external tissue fixation by fibroblast ingrowth through the pores and possibly also through the luminal anchoring of a non-thrombogenic biologically passivated surface.

The real challenge for vascular substitutes today is the small diameter (<4 mm) and/or low blood flow situation as is encountered in the femoral-popliteal region or more importantly in the coronary arteries. While patency rates run as high as 99% at 5 years in aortic grafts, femoralpopliteal grafts exhibit 50–70% patency at 5 years at best. Coronary artery replacement by prosthetic materials has barely been attempted.

Porous polytetrafluoroethylene tubing for use in vascular grafts is described in U.S. Pat. Nos. 3,962,153 and 3,953,566. U.S. Pat. No. 4,304,010 describes the application of a porous elastomeric coating over the outside surface of a stretched porous polytetrafluoroethylene tubing for use in vascular grafts. U.S. Pat. No. 4,321,211 describes incorporating an anticoagulant substance in a stretched porous polytetrafluoroethylene material and incorporating an outer porous elastomeric coating around the PTFE material containing a substance which counteracts the anticoagulant substance. U.S. Pat. No. 4,208,745 describes a stretched PTFE polymer in which the fibrous structure on the inside surface is made up of finer fibers than the fibrous structure on the outside surface. U.S. Pat. No. 4,193,138 describes the preparation and use of stretched porous PTFE materials in which the pores are filled with a water-insolubilized, water-soluble polymer, such as polyvinyl alcohol. U.S. Pat. No. 4,312,920 describes surface modification of polyurethane an alloy of silicone rubber, the material being useful in the fabrication of biomedical articles. U.S. Pat. No. 4,254,180 describes the preparation of a heparin-receptive surface on a mixture of a particulate resin and a graphite. U.S. Pat. No. 4,265,927 discloses heparinizing a charged surface of a biomedical article with a fine-grained, colloidal aqueous solution of a complex compound of heparin and a cationic sulfactant. U.S. Pat. No. 4,116,898 describes coating a polymeric substrate with a particular compound incorporating a heparin-like substance. U.S. Pat. No. 4,179,751 discloses the use of poly(alpha-olefin-sulfone) membrane prepared from $C_8$–$C_{18}$ alpha-olefins and sulfur dioxide for use in biomedical articles. U.S. Pat. No. 4,042,978 describes preparation of a plastic for prosthetics ma up of repeating units having the structure —$CH_2$—$CH_2$—O—. U.S. Pat. No. 3,853,062 describes use of a knitted linear polyester fabric which has been treated with a compacting solution for use as a vascular graft. U.S. Pat. No. 3,839,743 describes preparation of a thrombo-resistant article made by coating a surface in contact with blood with an organic polymeric material having fluoroalkyl side chains of the formula $C_nF_{2n+1}C_mH_{2m}$—. U.S. Pat. No. 4,167,045 describes the use of a woven Dacron material which has its surface modified to make it thrombo-resistant. U.S. Pat. No. 4,178,329 describes a graft copolymer of a particular type for use in fabrication of biomedical materials for biomedical uses. U.S. Pat. No. 4,047,252 describes a double-velour, synthetic vascular graft made of Dacron. U.S. Pat. No. 3,940,802 describes a blood bag fabricated from plasticized polyvinyl chloride and a thermoplastic polyester-based polyurethane. U.S. Pat. No. 4,319,363 describes a tube of collagenous tissue subjected to glutaraldehyde tanning to give cross-linked collagen fibrils for use as a vascular graft material.

A review of the safety and performance of currently available vascular prostheses can be found in Vol. 4, No. 4, *American Society for Artificial Internal Organs*, J. D. Mortensen, "Safety and Performance of Currently Available Vascular Prostheses." This article also references a comprehensive literature search performed for the Federal Food and Drug Administration by the Utah Biomedical Testing Laboratory on vascular grafts and their safety.

DISCLOSURE OF INVENTION

Figure 1:
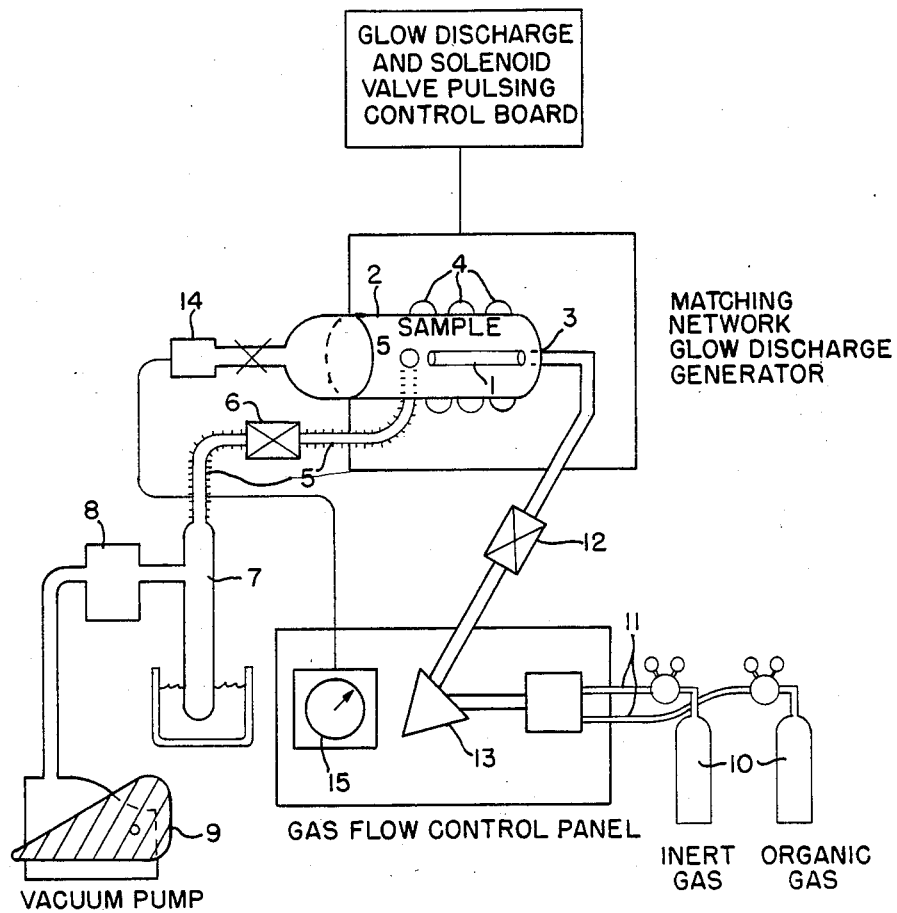
FIG. 1 is a schematic representation of the apparatus used in treating articles.
Figures 2, 2A:
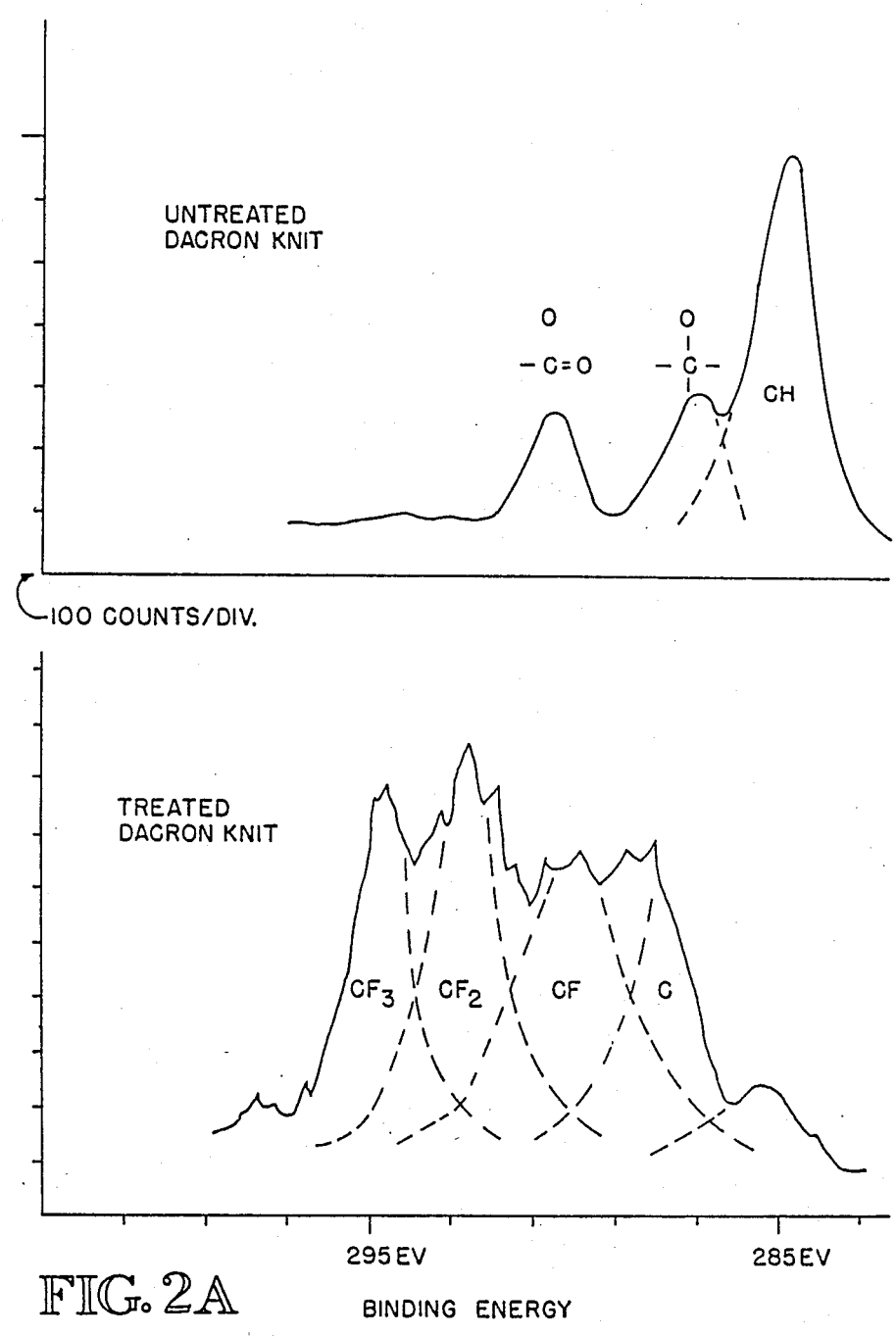
FIGS. 2 and 3 are graphic evaluations of treated and untreated prosthetic arterial grafts using the ESCA (electron spectroscopy for chemical analysis) technique.

It is an object of this invention to provide a method of treating substrate materials to improve their biocompatibility by exposure of the substrate material to plasma gas discharge in the presence of at least one gas capable of forming a biocompatible surface on the substrate exposed to the plasma gas discharge.

It is a further object of this invention to provide surface-modified biomedical articles and a method of making such articles which are thrombo-resistant and/or blood biocompatible over substantial periods of time.

It is a further object of this invention to provide articles whose surface is treated in a plasma gas discharge in the presence of one or more selected gases to improve the biocompatibility of the surface of the articles being treated.

It is a further object of this invention to provide vascular grafts and a method of making such by exposure of a vascular graft material to plasma gas discharge in the presence of at least one gas capable of rendering the surface of the graft in contact with blood or body tissue substantially thrombo-resistant and subject to reduced embolization over substantial periods of time.

It is a further object of this invention to provide vascular grafts whose interior surface exposed to blood is exposed to plasma gas discharge in the presence of one or more selected gases to render the surface in contact with the blood substantially thrombo-resistant over substantial periods of time without affecting the properties of the graft material, such as porosity, texture, area of surface contact, and mechanical properties.

These and other objects are accomplished by providing a substrate material and exposing the surface of the substrate material to plasma gas discharge in the presence of at least one gas capable of forming a biocompatible surface on the substrate in the form of a homogeneous, covalently bound, mechanically strong, ultra-thin layer.

BEST MODE FOR CARRYING OUT THE INVENTION

There is a need for biocompatible materials suitable for implants, blood contacting devices for diagnosis or therapy, vascular protheses, and other such articles which can be used over substantial periods of time, particularly when in contact with blood, which are substantially nonthrombogenic. There is also a need for vascular graft materials which can be used as femoral-popliteal or poplitealtibial arterial replacements and possibly in heart bypass operations where the necessary small diameter of the replacement causes difficulties with presently used prostheses because of their frequent tendency to block off rapidly with blood thrombus.

Providing organic surface coatings on substrate materials by means of plasma polymerization is known. An article by H. Yasuda, *J. Macromol. Sci.-Chem.*, A10(3), pp. 383–420 (1976), entitled "Plasma for Modification of Polymers," describes the effect of non-polymer-forming plasma on substrate materials and the effects of polymer-forming plasma on plasma-susceptible polymer substrates.

"Plasma," as used herein, is used in the sense of "low-temperature plasma" or "cold plasma" produced by glow discharges. Plasmas created by electric glow discharges contain a variety of species which are chemically active or energetic enough to cause chemical reactions, i.e., covalent bonding to a suitable substrate material. For example, electrons, ions of both charges, excited molecules at various levels of excitation, free radicals, and photons of various energies are created by cold plasma.

What is described herein is the deposition of certain gases as biocompatible polymers on clean surfaces of substrate materials for use as tissue implants or other orthopedic implants, blood-contacting devices for diagnosis and/or therapy, catheters, vascular graft materials, such as porous, knitted or woven Dacron materials other biomedically suitable materials. By "deposition" is meant the formation of a covalent bond between the substrate and the coating deposited on the substrate surface.

The substrate materials from which the biomedical articles of this invention may be made include a wide range of materials. Generally, synthetic resins are conventionally employed to fabricate articles. Such substrate materials are frequently fabricated from polyethylene, polyacrylics, polypropylene, polyvinyl chloride, polyamides, polystyrene, polyfluorocarbons, polyesters, silicone rubber, hydrocarbon rubbers, polycarbonates and other such synthetic resin materials. The substrate may be rigid or flexible, woven or nonwoven, molded or shaped, porous or nonporous. The substrate is first formed into a desired shape or configuration, depending on the use to which it is to be put, such as, for example, a valve, pin, catheter, sleeve, vascular graft, surgical tubing, etc. The surfaces of the substrate to be treated are then subjected to plasma gas discharge in the presence of at least one gas to form a homogeneous, tightly bound, mechanically strong, ultra-thin polymer layer on the surface of the substrate.

Preferably, plasma gas polymerization is carried out by positioning the substrate in a vacuum chamber, connecting the vacuum chamber to a source of gas and applying a high radio frequency energy to the substrate in the vacuum chamber by means of a suitable generator. When subjected to the glow discharge energy, the gas molecules present in the vapor are bombarded by electrons having high enough energy to rupture carbon-hydrogen bonds (about 4 eV), leading to the formation of free radicals and other chemical species.

From this point, polymerization is initiated, and a thin, uniform polymer film is deposited upon the substrate located within the vacuum chamber. Organic gases in the vapor state, like other gases, are ionized by bombardment with electrons under the discharge conditions, and such ions, when neutralized, have excess energy that leads to rapid polymerization. Solid films can be prepared from organic gases at rates of several ounces per KWH. The thickness can be controlled to within ±10 Å and is dependent on the concentration of the gas and the time to which the substrate is exposed to the plasma gas discharge.

Subjecting the substrate to glow discharge energy also affects the surface of the organic polymer substrate in contact with the low-temperature plasma gas. Energetic species from the organic polymer substrate surface break organic bonds with possible evolution of gaseous products, such as hydrogen, and formation of carbon-free radicals. These radicals lead to chemical reactions at the surface of the substrate and may result in surface cross-linking and modification of the surface properties of the substrate. The free radical sites formed on the substrate may also be employed directly to initiate polymerization with a new polymer bonded firmly to the substrate by carbon-carbon linkages.

Gases which may be used for forming a coating or film onto substrate materials include those capable of forming a biocompatible coating bonded to the substrate material in the presence of plasma gas discharge, such as gaseous hydrocarbons, halohydrocarbons, halocarbons and silanes. Specifically, tetrafluoroethylene, ethylene, and chlorofluoroethylene, may be used.

The parameters which define the system for plasma gas discharge include the gas itself, the flow rate of the gas, the initial system pressure, the geometrical design of the reactor, and the radio frequency or discharge power of the glow-discharge unit. The inductance or capacitance method of plasma discharge may be utilized, or other suitable method. Electrical energy is imparted to a neutral species, in this case the gas, to convert it to an active species. The plasma discharge also creates active species in the surface of the substrate material when a organic polymer resin substrate is used. The active gaseous species is covalently bonded to the substrate.

In the treatment of vascular graft materials to render them more biocompatible, particularly more blood compatible, it is preferable to initially clean the vascular graft material prior to exposure to plasma gas discharge with suitable solvents, followed by drying under vacuum. The graft material is then preferably subjected to plasma gas discharge at 5-100 watts energy in the presence of an atmosphere of inert gas, such as argon, for surface etching and activation of the substrate. This is followed by plasma gas discharge treatment at 5-100 watts energy in the presence of an atmosphere, of the gas to be deposited as a biocompatible coating bonded to the substrate material. The pressures utilized may vary but are generally within 0.10 to 10 torr. The treatment time the substrate is subjected to glow discharge may range from 5 minutes to one hour. The surface coating obtained is unirorm over the entire surface of the substrate, is non-leachable, and is repeatable.

The following examples are illustrative of the method and articles claimed but are not considered to be limiting.

FIG. 1 illustrates schematically the apparatus used for treating vascular graft materials. The vascular graft materials 1 were suspended within a glass reactor 2 in such a way that the gas used to modify the surface flowed into the reactor vessel at 3 and through the interior of the graft material 1. The reactor vessel was surrounded by a series of induction coils connected to a glow discharge generator. A gas outlet 5 in the reactor vessel was connected by flexible stainless steel tubing to an outflow solenoid valve 6 which, in turn was connected to a liquid nitrogen trap 7, backstreaming filter 8 and vacuum pump 9. Gas containing vessels 10 used to modify the surface of the vascular graft materials within the reactor vessel were connected to the reactor vessel by gas distributing pipes 11 with gas flow controlled by an inflow solenoid valve 12 and micrometer flow valve 13. A pressure sensor 14 connected to sense gas pressure within the reactor vessel was connected to a pressure meter 15.

Small diameter, vascular graft materials (4.5 and 5 mm ID) composed of woven or knitted velour Dacron (polyethylene terephthalate) were subjected to cleaning by 20-minute exposure in trichloroethylene to ultrasound in an ultrasonic cleaning apparatus, followed by a similar procedure in methanol and deionized water. The specific graft materials used included 4.5 mm ID Sauvage filamentous external velour grafts having mean porosities of 1420, 1917 and 2867 $cc/cm^2$-min, and 5 mm ID USCI DeBakey weave grafts with a porosity of 178 $cc/cm^2$-min.

The cleaned grafts were mounted in the reactor vessel, supported along the central longitudinal axis of a cylindrically designed glow-discharge glass reactor as previously described, and dried under vacuum to <0.01 torr. The reactor was flushed with argon gas for 5 minutes at 0.5 torr. With the argon pressure adjusted to 0.20 torr, the samples were reacted for 5 minutes in glow discharge at about 15 watts. The glow discharge was discontinued and argon allowed to continue flowing through the sample at 0.20 torr for 5 minutes. The plasma gas discharge resulted in surface etching and activation of the Dacron vascular graft materials by the argon. The argon gas was then displaced from the reactor vessel by tetrafluoroethylene gas. The samples were equilibrated in the tetrafluoroethylene atmosphere at 0.50 torr for 5 minutes and then subjected to a 30-minute glow discharge treatment at 0.20 torr tetrafluoroethylene and 15 watts energy. After the glow discharge treatment, the graft materials were maintained in the reactor vessel under the atmosphere of tetrafluoroethylene gas for about 4 hours. The resultant treated grafts had an interior surface which was highly fluorinated in a homogeneous, reproductible manner, as demonstrated by subsequent ESCA (electron spectroscopy chemical analysis) studies.

Figure 3:
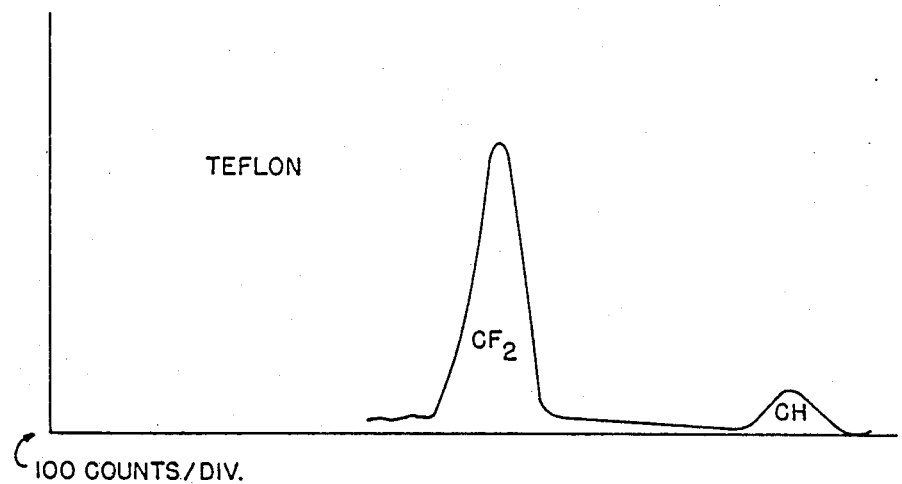
Figure 3A:
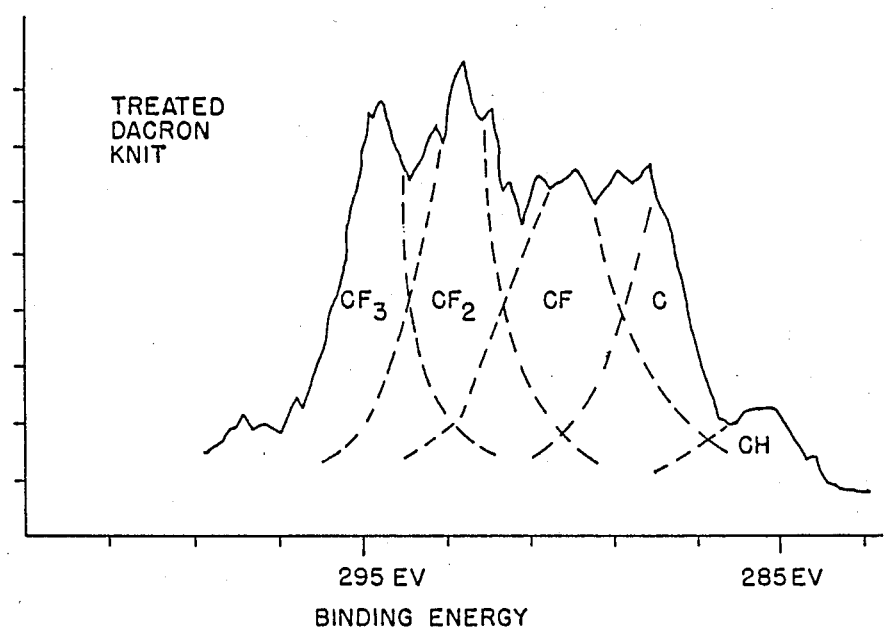
Figure 4:
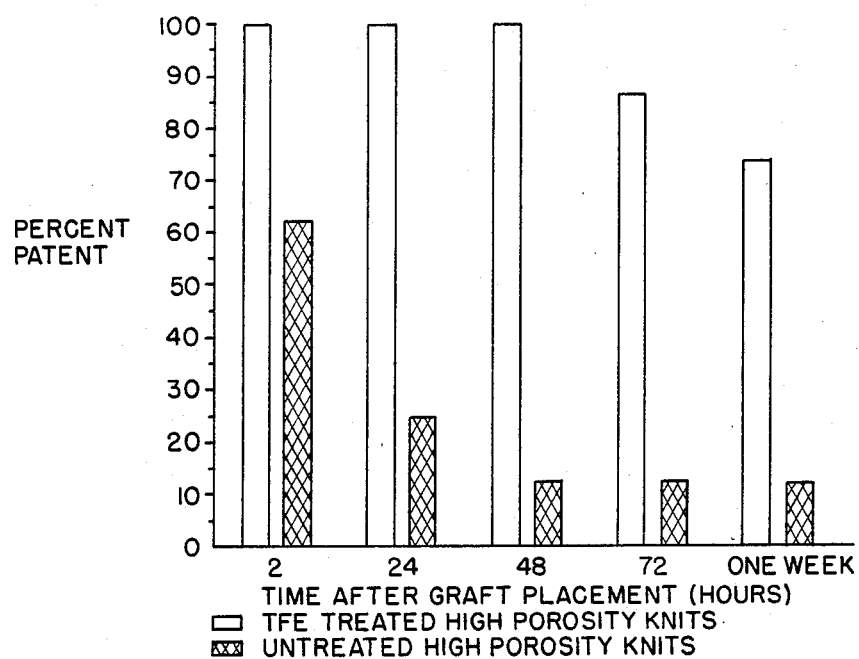
FIG. 4 is a graph of patency versus time of a 4.5 mm ID, high-porosity Dacron velour knit treated in accordance with this invention and a comparative untreated high-porosity Dacron velour knit in an ex vivo baboon femoral shunt research model.
Figure 5:
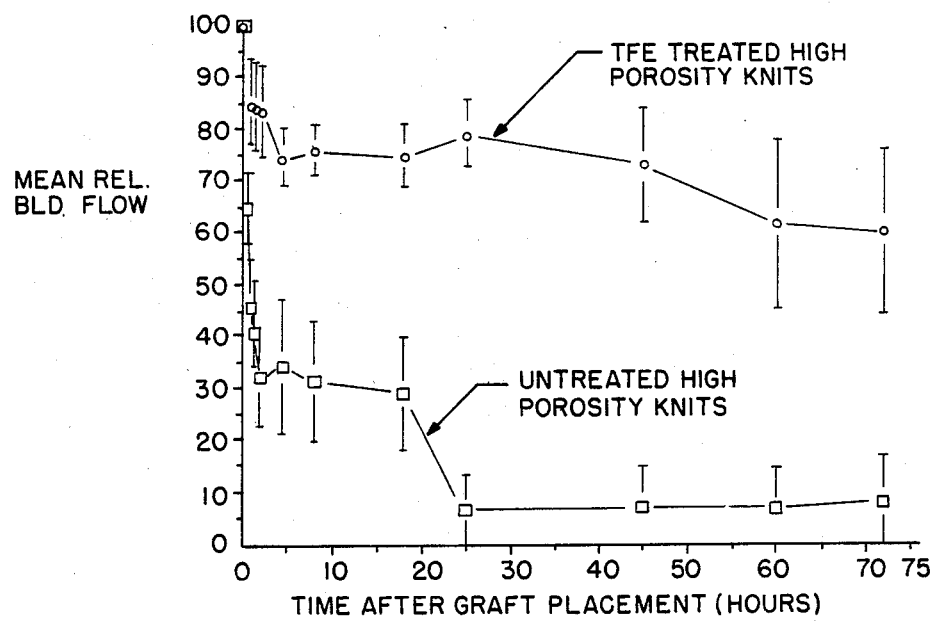
FIG. 5 is a graph of mean relative blood flow versus time of the same treated and untreated velour knits as in FIG. 4, again for the same baboon femoral shunt research model.

FIG. 3 illustrates ESCA spectra of glow discharge treated graft materials treated by the method previously described compared to the untreated graft materials. FIG. 4 illustrates ESCA spectra of glow discharge treated graft materials treated by the method previously described compared to "Teflon." The properties of the substrate material remained otherwise unchanged. The surface texture of the treated materials, as demonstrated by scanning microscopy, and the mechanical behavior of the vascular graft materials were not altered.

Similar vascular graft materials of Dacron were also treated solely by plasma gas discharge in an argon atmosphere at 0.20 torr for 10 minutes at 50 watts energy to modify the surface by activation and etching and subsequent oxidation of the etched material surface by exposure to the atmosphere.

The glow-discharge treated and control untreated grafts were placed in an ex vivo arterial-venous shunt connecting the cannulized femoral artery to the cannulized femoral vein of a baboon by means of a Silastic shunt. This ex vivo model possesses platelet, fibrinolytic and thrombogenic functions similar to humans. The graft materials were evaluated by measuring patency, flow rate, platelet consumption, platelet survival and graft platelet deposition during three time periods after graft placement:
(1) acute response (0–2 hours):
(2) steady state response (>1 day):
(3) passivated response (>/week)

The graphs (FIGS. 4–7) illustrate the average of several experiments of patentcy and mean relative blood flow vs. time of vascular graphs (tetrafluoroethylene treated, untreated and argon only treated) in an ex vivo baboon female shunt research model. Significantly improved patency and correspondingly improved flow were observed in tetrafluoroethylene-treated vascular grafts as compared with the untreated control Dacron grafts and the argon-etched only vascular grafts. The argon-etched only vascular grafts exhibited poorer patency and flow when compared with the untreated control vascular grafts.

Figure 6:
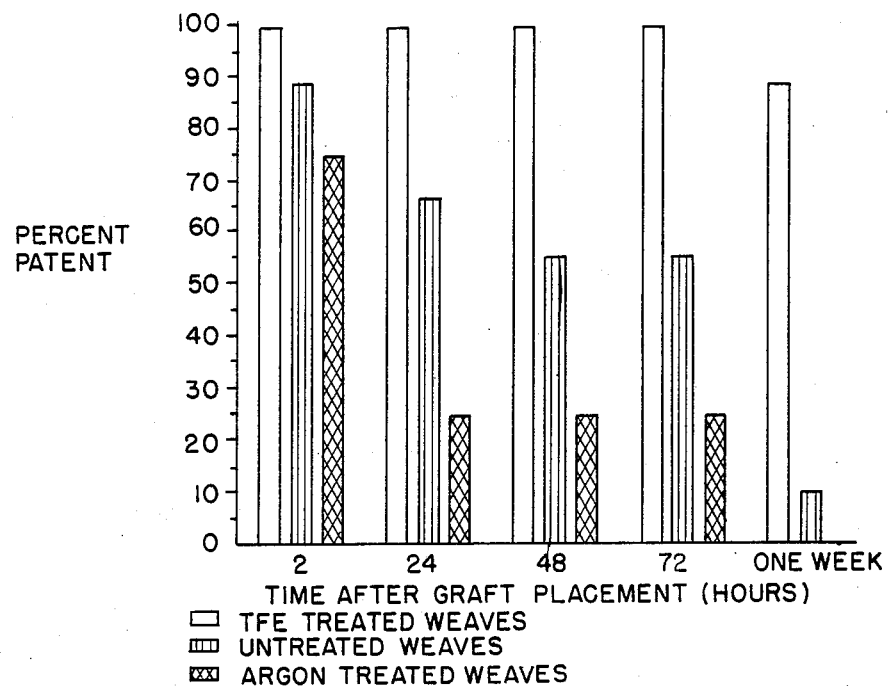
FIG. 6 is a graph of patency versus time of 5 mm ID Dacron weaves, one treated in accordance with the invention, a second untreated, and a third treated only with argon in an ex vivo baboon femoral shunt research model.
Figure 7:
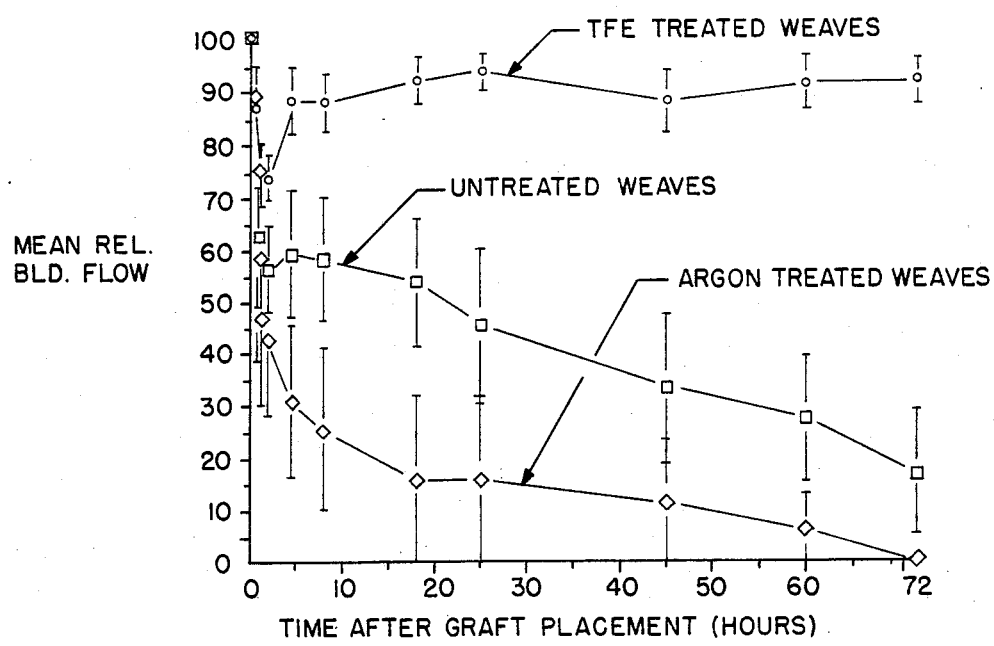
FIG. 7 is a graph of mean relative blood flow versus time of the same 5 mm ID Dacron weaves as in FIG. 6, again for the same baboon femoral shunt research model.

In particular, referring to FIG. 4, the 4.5 mm ID vascular grafts treated in accordance with the invention, after one week, exhibited an improved patency when compared to the untreated vascular grafts. In FIG. 6, the 5 mm ID-treated vascular grafts, after one week, exhibited an improved patency when compared to the untreated vascular grafts.

By means of a laser scattering detection technique it was determined that the untreated vascular grafts generated approximately 3 times more emboli than the tetrafluoroethylene-treated vascular grafts.

We claim:

1. A method of making a vascular prosthesis from a polymeric substrate material whose surface exposed to blood is treated to render it both thrombi- and emboli-resistant over extended periods of time, comprising:
exposing the surface of the substrate material to be exposed to blood to plasma gas discharge in the presence of a fluorinated hydrocarbon gas, whereby deposition occurs on said material, in the presence of the plasma gas discharge, forming a thin, covalently bound deposition on the surface of the material of a fluorocarbon polymer with short chain-length fluorocarbon polymer side or end groups without otherwise changing the mechanical behavior of the material or its surface texture.

2. The method according to claim 1, wherein said fluorinated hydrocarbon gas is present at a pressure of 0.10–1.0 torr, and said substrate and gas atmosphere are subjected to glow discharge energy ranging from 5–100 watts for a time ranging from 5 minutes to 1 hour.

3. The method according to claim 1, wherein the fluorinated hydrocarbon gas is tetrafluoroethylene.

4. A method of making a vascular prothesis from a polymeric substrate whose surface is treated to render it both thrombi- and emboli-resistant over extended peiods of time, said treatment comprising:
exposing the material to plasma gas discharge in the presence of a fluorinated hydrocarbon gas;
discontinuing the plasma gas discharge; and
allowing the material to remain in the atmosphere of the halocarbon gas, whereby deposition of a fluorocarbon polymer with short chain-length fluorocarbon polymer side or end groups on said plasma exposed surfaes results.

5. The method of claim 4 wherein the vascular prosthesis material is woven polyethylene terephthalate.

6. The method of claim 4 wherein the vascular prosthesis material is a porous fluorohydrocarbon and the fluorinated hydrocarbon gas is tetrafluoroethylene.

7. The method of claim 4 wherein the fluorinated hydrocarbon gas is tetrafluoroethylene.

8. A surface modified vascular graft material whose treated surface, when exposed to blood, is both thrombi- and emboli-resistant over extended periods of time, comprising:
a fabric of polyethylene terephthalate material having a thin, covalently bonded coating on the surface thereof composed principally of a fluorocarbon polymer with short chain-length fluorocarbon side or end groups resulting from an electric glow discharge polymerization process conducted in a fluorinated hydrocarbon gaseous atmosphere.

9. A method of making surface modified articles of a polymeric substrate material whose modified surface, when exposed to blood, is both thrombi- and emboli-resistant over extended periods of time, comprising:
exposing the surface of the substrate material to plasma gas discharge in the presence of at least one fluorinated hydrocarbon gas, forming a thin, covalently bonded coating on the substrate material consisting of fluorocarbon polymer with side or end groups of less than three carbon atoms in chain length.

10. A biomedical article made by the method of claim 9.

11. The method of claim 9, including cleaning and drying the substrate material under vacuum prior to exposure to the plasma gas discharge.

12. The method of claim 9, wherein the plasma gas discharge is generated by applying high radio frequency energy to a substrate contained in a reactor vessel.

13. The process of claim 12 wherein the high radio frequency energy applied ranges from 5–50 watts and wherein the presence of the gas within the reactor vessel ranges from 0.10 to 1.0 torr.

14. A method of making surface modified substrate materials whose modified surface, when exposed to blood, is both thrombi- and emboli-resistant over extended periods of time, comprising:
exposing the substrate material to plasma gas discharge in the presence of an inert gas for a period of time sufficient to etch and activate the surface of the substrate; and
exposing the substrate material to plasma gas discharge in the presence of a fluorinated hydrocarbon gas, whereby chemical deposition in the presence of the plasma discharge results in a fluorocarbon polymer with short chain-length fluorocarbon polymer side or end groups deposited on the substrate as a thin, covalently bound deposition, the plasma discharge causing ionization of the gas molecules, partial reaction of the ionized molecules to generate polymer molecules, and condensation of the polymer molecules on the substyrate to form a covalently bound deposition on the subatrate without otherwise changing the mechanical behavior of the substrate material or its surface texture.

15. The method of claim 14 wherein said inert gas is argon and said fluorinate hydrocarbon is tetrafluoroethylene.

* * * * *